United States Patent
Grass et al.

(10) Patent No.: US 7,142,628 B2
(45) Date of Patent: Nov. 28, 2006

(54) COMPUTED TOMOGRAPHY METHOD

(75) Inventors: Michael Grass, Buchholz in der Nordheide (DE); Thomas Koehler, Norderstedt (DE); Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/509,932

(22) PCT Filed: Apr. 9, 2003

(86) PCT No.: PCT/IB03/01284

§ 371 (c)(1),
(2), (4) Date: Jun. 27, 2005

(87) PCT Pub. No.: WO03/085390

PCT Pub. Date: Oct. 16, 2003

(65) Prior Publication Data
US 2005/0243962 A1 Nov. 3, 2005

(30) Foreign Application Priority Data
Apr. 11, 2002 (DE) .................................. 102 15 890

(51) Int. Cl.
*G01N 23/00* (2006.01)

(52) U.S. Cl. .......................................... 378/4; 378/901
(58) Field of Classification Search .................... 378/4, 378/8, 15, 19, 901
See application file for complete search history.

(56) References Cited

U.S. PATENT DOCUMENTS

| | | | |
|---|---|---|---|
| 5,406,479 A | 4/1995 | Harman | |
| 5,960,056 A | 9/1999 | Lai | |
| 6,275,561 B1 * | 8/2001 | Danielsson | 378/15 |
| 6,285,733 B1 | 9/2001 | Proksa et al. | |
| 6,317,478 B1 | 11/2001 | Patch | |
| 6,785,356 B1 * | 8/2004 | Grass et al. | 378/4 |
| 2001/0038678 A1 * | 11/2001 | Grass et al. | 378/4 |

OTHER PUBLICATIONS

Kachelriess, Marc, et al.; Advanced single-slice rebinning in cone-beam spiral CT; Medical Physics; vol. 27, No. 4, No. 4, 2000, pp. 754-772.

* cited by examiner

*Primary Examiner*—Courtney Thomas

(57) ABSTRACT

The invention relates to a computed tomography method in which a rebinning operation is carried out so as to form parallel fan beams whose rays traverse a plane, containing the axis of rotation, in equidistant puncture points. Reconstruction is performed for rays which extend perpendicularly to said planes. Such a transition from a cone beam geometry to a parallel beam geometry enables very fast reconstruction which can be carried out notably for CT fluoroscopy.

6 Claims, 4 Drawing Sheets

COMPUTED TOMOGRAPHY METHOD

BACKGROUND

The invention relates to a computed tomography method in which an examination zone is irradiated by means of a conical radiation beam and in which the radiation source which generates the radiation beam rotates along a circular trajectory around an axis of rotation relative to the examination zone. The invention also relates to a computed tomography apparatus for carrying out the method as well as a computer program for controlling the computed tomography apparatus.

A method of this kind and a corresponding computed tomography apparatus are known from U.S. Pat. No. 6,285,733. The measuring values which are acquired therein by a two-dimensional detector unit are dependent on the intensity in the radiation beam to the other side of the examination zone and are first subjected to a rebinning operation. This operation yields groups of measuring values which are associated with fan beams which are situated in equidistant fan beam planes which extend parallel to one another and to the axis of rotation. After the rebinning operation, the fan beans are composed of rays which traverse a plane, containing the axis of rotation and extending perpendicularly to the fan beam planes of the relevant group, in puncture points which are situated on equidistant connecting lines which extend perpendicularly to the axis of rotation and parallel to one another.

The measuring data produced by the rebinning operation are subsequently subjected to one-dimensional high-pass filtering as well as to backprojection in order to form at least one CT image. The reconstruction of a voxel in the examination zone then takes into account from each group the measuring data of rays having traversed the relevant voxel from different directions. If the voxel is not situated in the central plane defined by the circular trajectory, the rays traverse the voxel at an angle relative to the central plane and each ray traverses the plane associated with its group at an angle other than 90°. The reconstruction taking into account this cone beam geometry is comparatively complex and hence requires a comparatively large amount of calculation time.

For various applications, however, shorter calculation times are desired. This is the case, for example, in CT-guided biopsy (CT=computed tomography), where a biopsy needle is introduced into an object to be examined and the advancing of the biopsy needle is continuously checked on the basis of a series of three-dimensional CT images. In such so-called CT fluoroscopy only very little time is available for the reconstruction of a CT image, notably when use is made of a so-called "sliding-window" technique in which a CT image is updated (while taking into account newly acquired CT data and CT data already used for the reconstruction of the previous CT image) within a period of time which is significantly shorter than the period of time required for the acquisition of the measuring data of a complete CT image.

SUMMARY

Therefore, it is an object to conceive a method of the kind set forth in such a manner that the time required for the reconstruction of a CT image is reduced. This object is achieved by means of a computed tomography method which includes the steps of:

a) generating, while using a radiation source, a conical radiation beam which traverses an examination zone or an object present therein, b) generating a circular relative motion, including a rotation about an axis of rotation, between the radiation source on the one side and the examination zone or the object on the other side, c) acquiring, while using a detector unit, measuring values which are dependent on the intensity in the radiation beam to the other side of the examination zone during the relative motion, d) rebinning the measuring values so as to form a number of groups, each group containing the measuring values of fan beams which are situated in equidistant fan beam planes which extend parallel to one another and to the axis of rotation and are composed of rays which traverse a plane which contains the axis of rotation and extends perpendicularly to the fan beam planes of this group in puncture points which are situated on equidistant connecting lines which extend perpendicularly to the axis of rotation and parallel to one another, e) reconstructing the spatial distribution of the attenuation of the X-rays from the measuring data, formed by the rebinning of the measuring values, for rays which extend perpendicularly to the planes of the groups and through the puncture points so as to form at least one CT image.

Whereas the reconstruction according to the known method takes place while taking into account the cone beam geometry prevailing during the acquisition of the measuring values, the present reconstruction is based on a parallel beam geometry in which all beams extend perpendicularly to the plane of the associated group and hence parallel to the central plane defined by the circular trajectory. The amount of calculation work required for such a parallel beam geometry is substantially smaller than that required for a cone beam geometry. A further advantage resides in the fact that in accordance with the invention a cylindrical part of the examination zone is reconstructed.

Because the cone angle of the rays (being the angle enclosed by the rays relative to a plane perpendicular to the axis of rotation) is de facto ignored, the examination zone outside the central plane cannot be exactly reconstructed; this also holds for the known method, be it for different reasons. The loss of image quality, however, is small if the detector unit comprises only few detector lines or if the maximum cone angle is small. The image quality is notably higher than in the case of a method in which the measuring values are treated from the very start as values from parallel planes in which each time one detector line is situated.

The claims 2 and 3 define proven methods for the reconstruction of a CT image in the case of a parallel beam geometry. Such methods per se enable exact reconstruction of the examination zone, be it that the reconstruction is exact only within the central plane, because the parallel beam geometry on which the reconstruction is based occurs only in the central plane during the acquisition of the measuring values.

Claim 4 describes a preferred CT fluoroscopy application for fast reconstruction of the CT images, notably if the distances in time between two updates of a CT image are shorter than the period of time for complete acquisition of the measuring values for a CT image.

Claim 5 describes a computed tomography apparatus for carrying out the method and claim 6 describes a computer program for controlling a computed tomography apparatus of this kind.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
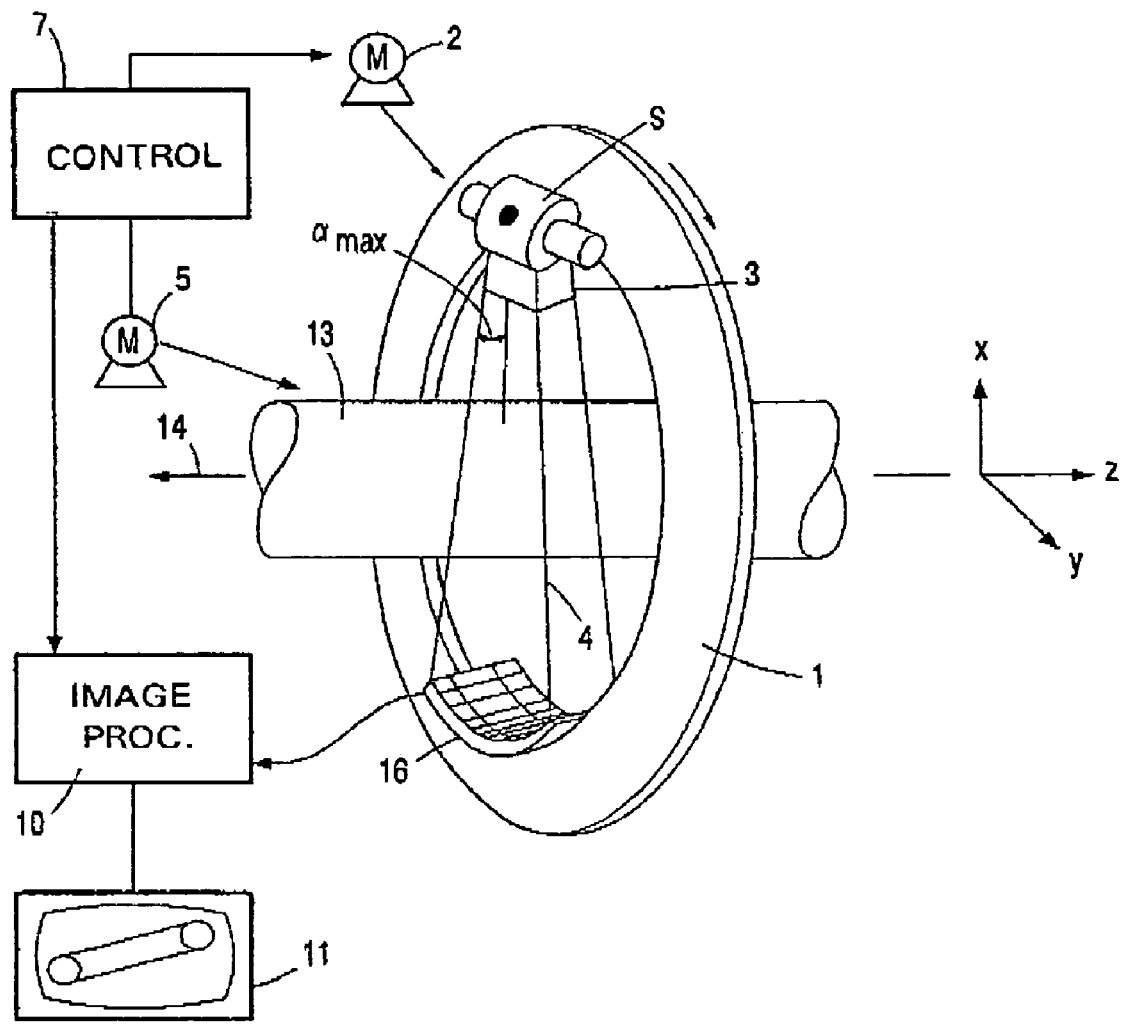
FIG. 1 shows a computed tomography apparatus which is suitable for carrying out the invention.

The computed tomography apparatus shown in FIG. 1 includes a gantry 1 which is capable of rotation about an axis of rotation 14 which extends parallel to the z direction of the co-ordinate system shown in FIG. 1. To this end, a motor 2 drives the gantry at a preferably constant but adjustable angular speed. A radiation source S, for example, an X-ray source, is connected to the gantry. The source is provided with a collimator device 3 which forms a conical radiation beam 4 from the radiation produced by the radiation source S, that is a radiation beam which has a finite dimension other than zero in the z direction as well as in a direction perpendicular thereto (that is, in a plane perpendicular to the axis of rotation).

The radiation beam traverses an examination zone 13 in which an object to be examined, for example, a patient on a patient table (both not being shown), may be situated. The examination zone 13 has the shape of a cylinder. After having traversed the examination zone 13, the X-ray beam 4 is incident on a two-dimensional detector unit 16 which is connected to the gantry 1. The detector unit comprises a number of detector lines which are situated adjacent one another in the z direction and each of which comprises a plurality of detector elements. The detector lines are situated in planes perpendicular to the axis of rotation and on an arc of circle around the radiation source S; however, they may alternatively describe an arc of circle around the axis of rotation 14 or be straight. Each detector element provides a measuring value for a ray of the radiation beam 4 in each position of the radiation source.

The angle of aperture of the radiation beam, denoted by the reference $\alpha_{max}$ (the angle of aperture is defined as the angle enclosed by a ray, situated at the edge of the radiation beam 4 in a plane perpendicular to the axis of rotation, relative to the plane of the central ray defined by the radiation source S and the axis of rotation 14), determines the diameter of the cylinder within which the object to be examined is situated during the acquisition of the measuring values. The examination zone 13, or the object to be examined or the patient table, can be displaced parallel to the axis of rotation 14 by means of a motor 5. When the motors 5 and 2 are simultaneously activated, the radiation source S and the detector unit 16 perform a helical motion around the examination zone 13. However, when the motor 5 for the transport in the z direction is stationary and the motor 2 rotates the gantry separately, the radiation source S and the detector unit 16 perform a circular scanning motion relative to the examination zone 13.

The measuring data acquired by the detector unit is applied to an image processing computer 10 which reconstruct therefrom the absorption distribution in a part of the examination zone 13 and, for example, displays it on a monitor. The two motors 2 and 5, the image processing computer 10, the radiation source S and the transfer of the measuring values from the detector 16 to the image processing computer 10 are controlled by way of a suitable control unit 7.

Figure 2:
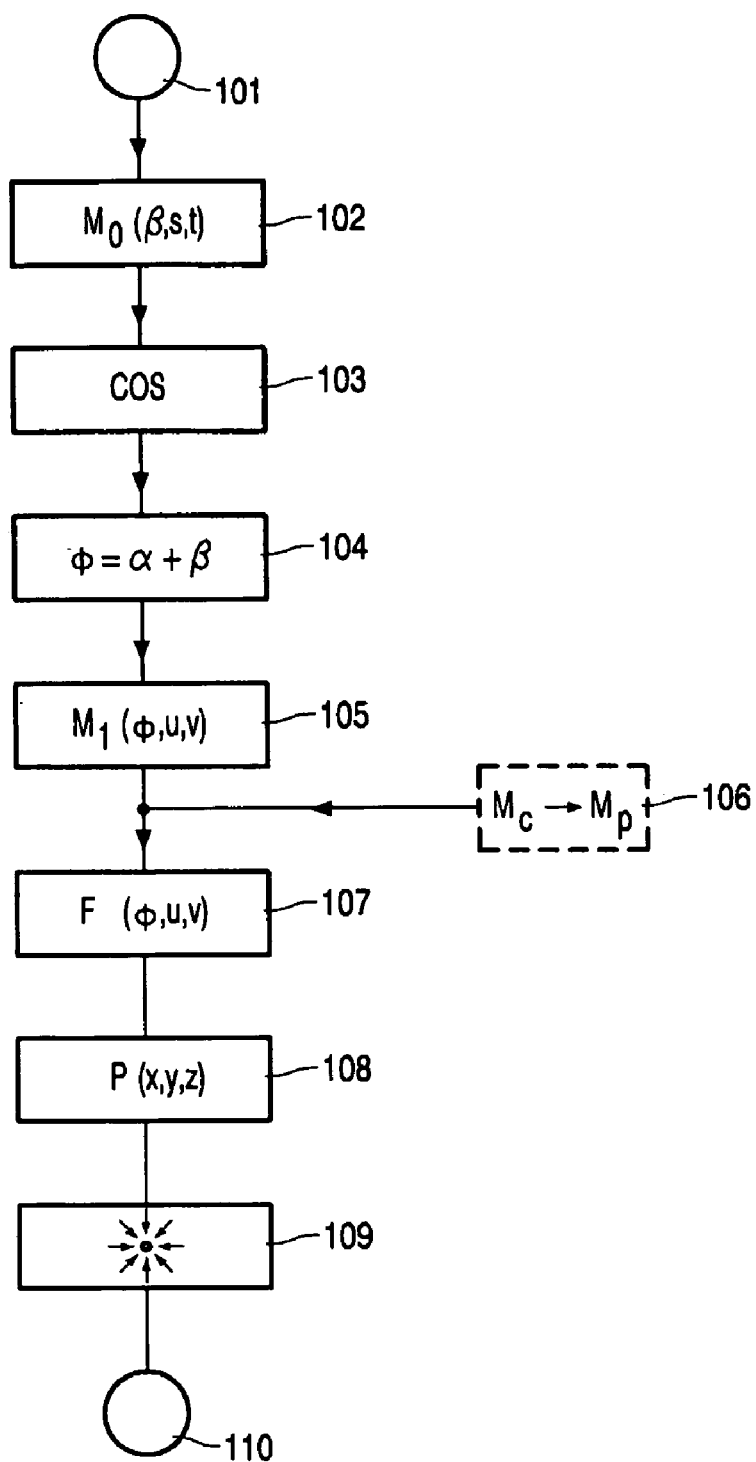
FIG. 2 shows a flow chart of the method in accordance with the invention.

FIG. 2 illustrates the execution of an acquisition and reconstruction method which can be carried out by means of the computed tomography apparatus shown in FIG. 1.

After the initialization in block 101, the gantry rotates at a constant speed, the duration of one revolution being 1 second or less. The radiation source S emits a conical radiation beam which traverses the examination zone and the measuring values acquired by the detector elements of the detector unit 16 are buffered in the image processing computer 10 so as to be further processed.

Figure 3:
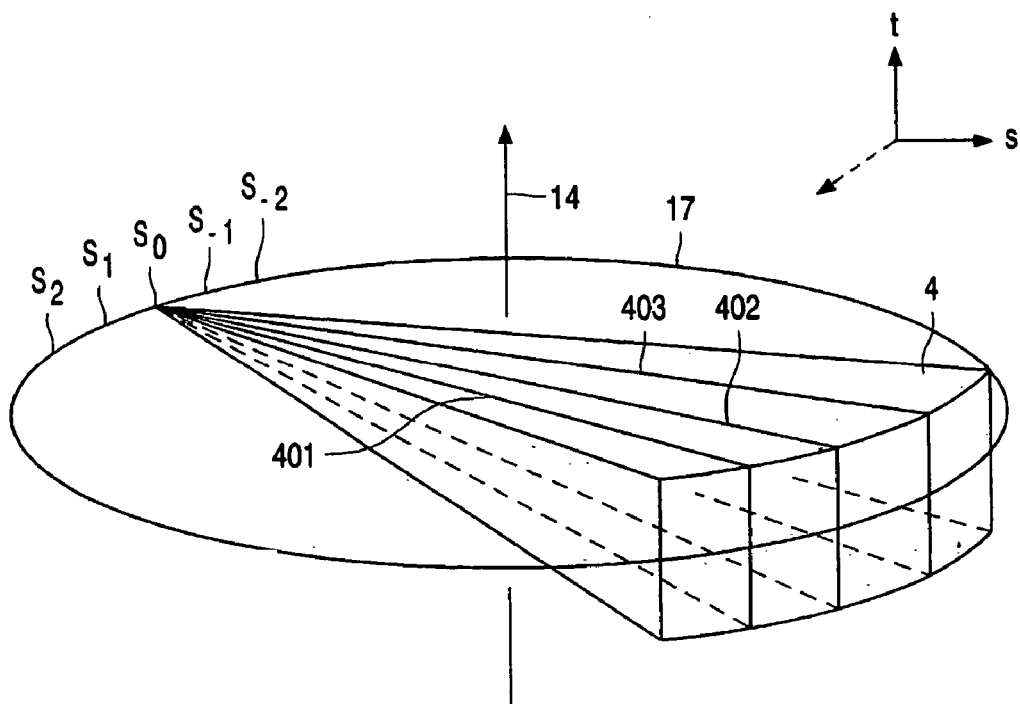
FIG. 3 shows a conical radiation beam generated in a radiation source position.

FIG. 3 shows the circular trajectory described around the axis of rotation 14 by the radiation source S and the detector unit 16. The trajectory 17 is situated in a plane which is perpendicular to the axis of rotation and which will be referred to hereinafter as the central plane. The Figure shows a radiation beam 4 which is emitted by the radiation source in a given radiation source position $S_0$. This conical radiation beam can be decomposed into a plurality of flat fan beams which are situated, like the fan beams 401, 402, 403 shown in FIG. 3, in planes extending parallel to the axis of rotation 14. The fan beams emanate from the same radiation source position and are detected by a respective column of detector elements on the detector unit 16, said column extending parallel to the axis of rotation 14.

FIG. 3 indicates that the emitted conical radiation beam is also measured in other positions of the radiation source, for example, $S_{-2}, S_{-1}, S_1$ or $S_2$. These radiation source positions, or the radiation beams emitted therein, can be characterized by a parameter $\beta$ which corresponds to the angle enclosed by the normal from the radiation source position to the axis of rotation 14 relative to a reference line in the central plane ($\beta$ may be larger than $2\pi$ in conformity with the number of revolutions of the radiation source around the axis of rotation). The position of each fan beam in a radiation beam can be characterized by a parameter s which describes the position of the column of detector elements, being struck by the fan beam, within the detector unit 16. Each ray within such a fan beam itself can be characterized by the parameter t which describes the position of the detector element, being struck by the relevant ray, within the column of detector elements, or the distance between this detector element and the central plane.

The acquired measuring values form in this manner a three-dimensional data set $M_0(\beta, s, t)$, each measuring value corresponding to a grid point of a regular Cartesian grid in a three-dimensional ($\beta$, s, t) parameter space. The acquisition of the measuring values thus constitutes a sampling of the so-called object function (in this case of the line integral of the attenuation of the radiation) at a number of points which are regularly distributed in the ($\beta$, s, t) parameter space.

The acquisition of the measuring values in the step 102 and the processing of these measuring values in the subsequent steps 103 and further take place in parallel in time, so that the acquired measuring values can already be further processed while further measuring values are still being acquired.

In the step 103 the measuring values are multiplied by the cosine of the angle enclosed by the ray, along which the measuring value was acquired, relative to a plane perpendicular to the axis of rotation. If the dimensions of the detector unit are small in the z direction, however, this step can be dispensed with, because in that case the angle is so small that the cosine of the angle is practically always 1.

The data set $M_0(\beta, s, t)$, acquired in the step 102 and possibly modified in the step 103, is not yet optimum for further processing. Therefore, in the steps 104 and 105 a so-called rebinning of the measuring values is carried out. The data is then resorted and re-interpolated as if it had been measured with a different radiation source (a circular radiation source emitting mutually parallel fan beams) and with a different detector (a flat, rectangular detector containing the axis of rotation). To this end, in the step 104 first the fan beams which are situated in planes which are parallel to one another and to the axis of rotation 14 and emanate from different radiation source positions are combined so as to form respective groups.

Figure 4:
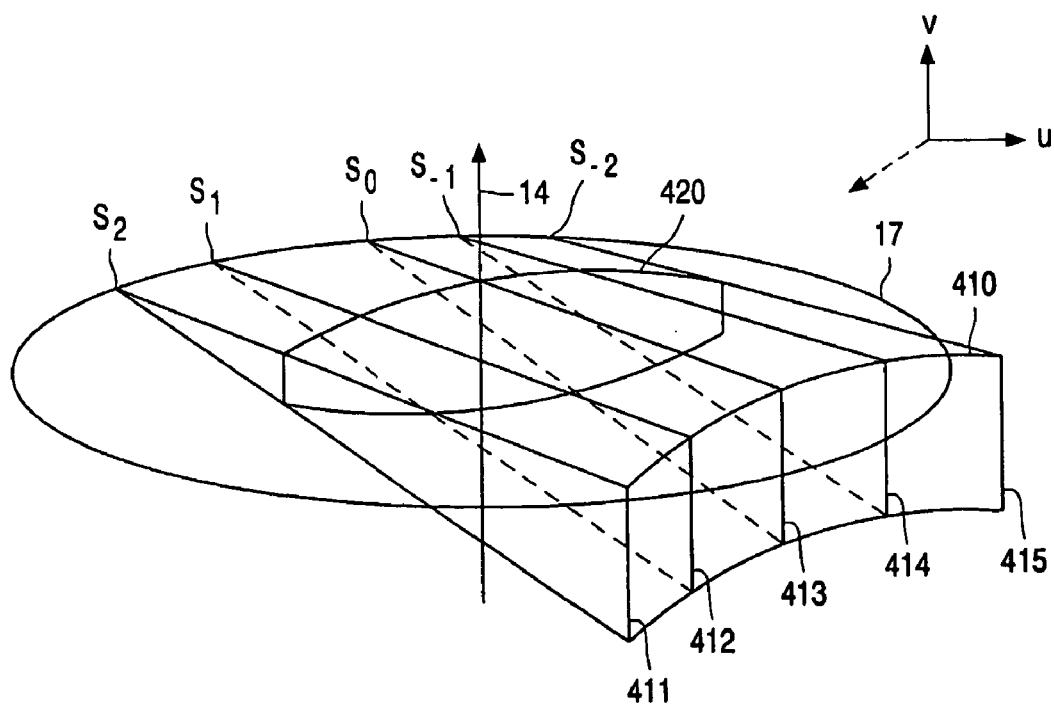
FIG. 4 shows the fan beams formed by the rebinning in parallel planes.

FIG. 4 shows a group of fan beams formed in this manner. Each time one fan beam of each radiation source position $S_{-2} \ldots S_0 \ldots S_2$ belongs to such a group. The fan beams associated with a group satisfy the condition:

$$\phi = \alpha + \beta \qquad (1)$$

Therein, $\phi$ is the projection direction in which a group of fan beams extends through the examination zone. $\alpha$ is the angle enclosed by the relevant fan beam in the original radiation beam (see FIG. 3) relative to a plane which is defined by the axis of rotation 14 and the radiation source position (for example, $S_2$ which itself is defined by the angle $\beta$). Groups of fan beams of this kind are formed for different projection directions $\phi$ which deviate from one another each time by a given projection angle increment $d\phi$. When the fan beams of a radiation beam do not exactly satisfy the equation (1), a corresponding fan beam must be determined by interpolation from the rays of fan beams neighboring the fan beam 4 (FIG. 3).

The fan beams of a group, including the fan beams 411 . . . 415 shown in FIG. 4, define a radiation beam 410 which has a tent-like shape and is composed of fan beams which are situated in planes which extend parallel to one another and parallel to the axis of rotation. FIG. 4 also shows the area of intersection 420 which is obtained when the radiation beam 410 is intersected by a plane which contains the axis of rotation 14 and extends perpendicularly to the planes of the fan beams 411 . . . 415. The upper and lower edges are curved outwards in the form of a cushion, because the radiation source positions at the center are situated further from the plane of intersection than the radiation source positions at the edge.

Figure 5:
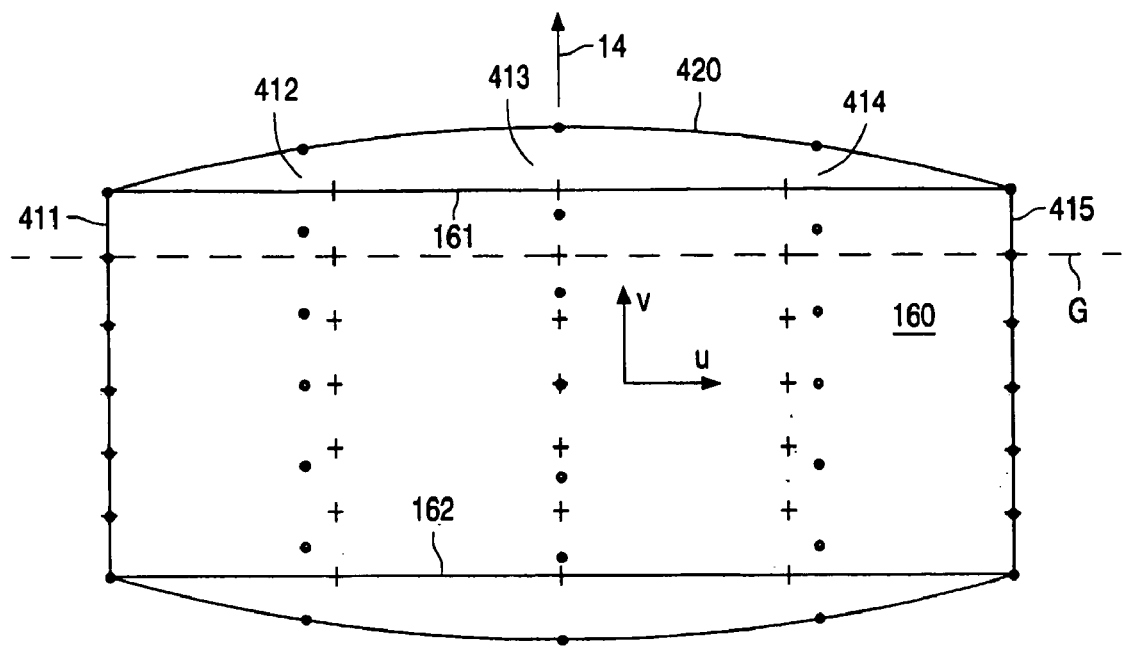
FIG. 5 is a cross-sectional view of these fan beams.

FIG. 5 is a detailed representation of the area of intersection 420. Round dots mark the positions in which the rays of the fan beams 411 . . . 415 puncture the area of intersection. For the outer fan beams 411 and 415 these dots are situated nearer to one another than for the inner fan beams 412 . . . 414, and in one of the inner fan beams (for example, 413) the distance between these points decreases in the direction from the center towards the edge. The area of intersection 420 contains a rectangular area 160 whose upper edge 161 and lower edge 162 are given by the dimensions of the two outer fan beams 411 and 415 in the area of intersection 420 and which will also be referred to as "virtual detector" hereinafter.

In the step 105 the rays of the fan beams 411 . . . 415 of a group are calculated again by interpolation, that is, in such a manner that they traverse the virtual detector 160 in puncture points which are situated on mutually parallel, equidistant connecting lines which extend perpendicularly to the axis of rotation 14. The distance between the puncture points on each connecting line is constant. The puncture points resulting from this rebinning step are marked by a symbol "+" in FIG. 5 and one of the connecting lines extending parallel to the edges 161 and 162 is represented by the dashed line G in FIG. 5.

The two rebinning steps 104 and 105 transform in this manner the measuring values $M_0(\beta, s, t)$, defined by a regular grid in the $(\beta, s, t)$ parameter space, into measuring values $M_1(\phi, u, v)$ which are defined by a regular grid in a three-dimensional $(\phi, u, v)$ parameter space. The parameters u and v represent the co-ordinates of the puncture points in the direction perpendicular to and parallel to the axis of rotation, respectively, in the virtual detector 160. The values $M_1(\phi, u, v)$ produced by the rebinning operation will be referred to as measuring data hereinafter so as to distinguish them from the measuring values $M_0(\beta, s, t)$ produced by the measurement.

Because the rays extending through the area of intersection 420 above the upper edge 161 and below the lower edge 162 are not used for the remaining part of the method, it is advantageous to configure the collimator arrangement 3 (FIG. 1) in such a manner that the conical radiation beam does not contain these rays. Instead of straight edges extending perpendicularly to the axis of rotation, the collimator arrangement 3 should have edges curved inwards for this purpose. The radiation load for the patient would thus be reduced.

Figure 6:
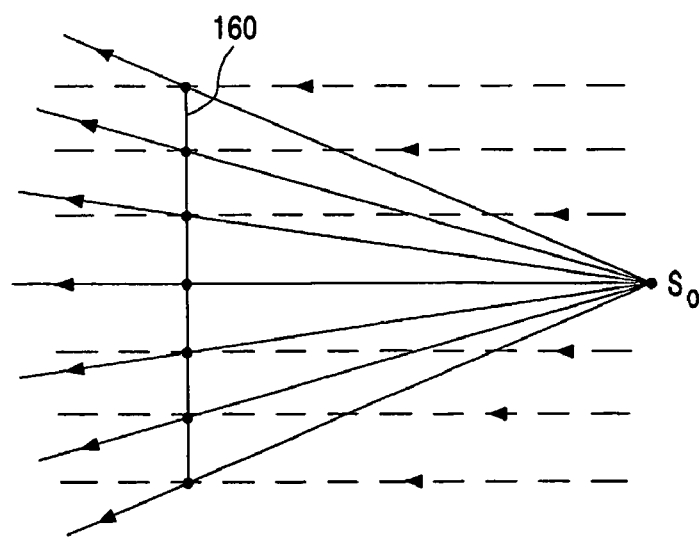
FIG. 6 shows the cone beam geometry and the parallel beam geometry.

The invention as described so far with reference to FIG. 2 is known from U.S. Pat. No. 6,285,733. In accordance with the invention, however, the further processing of the measuring data is not carried out on the basis of a cone beam geometry but on the basis of a parallel beam geometry. This difference in processing is symbolically represented by the dashed box 106 and illustrated in FIG. 6. The solid lines in FIG. 6 represent the diverging rays of a fan beam (for example, 413) emanating from a radiation source position (for example, $S_0$). These rays traverse the virtual detector 160 in equidistant puncture points. The invention, however, instead utilizes the rays which are represented by dashed lines and are incident perpendicularly on the virtual detector 160. The measuring data produced by the rebinning operation are associated with the parallel rays traversing each time the same puncture point of the virtual detector 160 as the diverging rays emanating from the radiation source position $S_0$.

This transition to parallel rays does not require a separate calculation step (which is why the box 106 is denoted only by dashed lines), because it is merely necessary to ignore the cone angle (being the angle enclosed by the rays relative to a plane perpendicular to the axis of rotation 14). A multi-slice method, in which the data is acquired in parallel slices, then enables reconstruction by taking into account the measuring data of rays which are situated each time in the same plane, perpendicular to the axis of rotation 14, so as to reconstruct the slices independently of one another.

The invention thus enables the reconstruction of a cylindrical part of the examination zone whose height corresponds to the distance between the two edges 161 and 162 of the virtual window 160. The height h of the cylindrical part of the examination zone is in conformity with the relation:

$$h = r \tan(\gamma_{max})\cos(\alpha) \quad (1)$$

Therein, r is the radius of the circular trajectory 17, $\gamma_{max}$ is the maximum cone angle and $\alpha$ is the fan angle, that is, the angle of aperture of the radiation beam in a plane perpendicular to the axis of rotation.

In the geometrical conditions described above, a reconstruction is performed by a filtered backprojection in the steps 107 to 109. In the step 107 a one-dimensional ramp-like filtering of the measuring data $M_1(\theta, u, v)$ is carried out. All measuring data having the same projection angle $\theta$ and the same parameter v are then subjected to a filtering operation during which the transfer factor increases ramp-like as a function of the frequency.

The data $F(\theta, u, v)$ thus filtered is then subjected to backprojection. In the step 108 a voxel $P(x, y, z)$ is defined. In the subsequent step 109 the contributions to the attenuation value of the relevant voxel by measuring data whose associated rays traverse the voxel from different projection directions $\phi$ and are situated in the same plane parallel to the central plane as the voxel are determined and summed. This is repeated for all voxels in said plane, so that the object function for this plane is known. The steps 108, 109 are carried out for all planes parallel to the central plane and the voxels and rays present in these respective planes. Subsequently, the CT image reconstructed in this manner can be displayed (step 110).

In the case of a fluoroscopic computed tomography method the steps 101 to 110 form part of a continuous acquisition and reconstruction process during which continuously new measuring values and new CT images of the examination zone are formed. The distance in time between updates of a CT image can then be shorter than the period of time required by the computed tomography apparatus so as to acquire measuring values for a complete CT image. In this case the reconstruction of the CT image takes place partly from measuring values which are acquired anew and partly from measuring values which have already been used for the reconstruction of the preceding CT image.

Instead of using a filtered backprojection in the steps 107 to 109, the spatial distribution of the attenuation in the planes defined by the puncture points can also be determined by means of an inverse Fourier transformation after the measuring data have first been transformed on a Cartesian grid in the individual planes by means of a gridding method.

The invention has been described with reference to the preferred embodiments. Modifications and alterations may occur to others upon reading understanding the preceding detailed description. It is intended that the invention be constructed as including all such modifications and alterations insofar as they come within the scope of the appended claims or the equivalents thereof.

The invention claimed is:

1. A computed tomography method which includes the steps of:
    a) generating a conical radiation beam which traverses an examination zone or an object present therein,
    b) rotating the conical radiation beam relative to the examination zone or the object about an axis of rotation,
    c) acquiring measuring values which are dependent on the intensity in the radiation beam on the other side of the examination zone during the relative rotation,
    d) rebinning the measuring values so as to form a number of groups, each group containing the measuring values of fan beams which are situated in equidistant fan beam planes which extend parallel to one another and to the axis of rotation and are composed of rays which traverse a plane which contains the axis of rotation and extends perpendicularly to the fan beam planes of this group in puncture points which are situated on equidistant connecting lines which extend perpendicularly to the axis of rotation and parallel to one another,
    e) reconstructing the measuring values representing the fan beams of rays in the fan beam planes by treating the measuring values as representing rays which extend parallel to each other and perpendicularly to the transverse plane through which the puncture points are defined to form at least one CT image.

2. A computed tomography method as claimed in claim 1, in which the reconstruction step comprises:
    a) one-dimensional filtering of the measuring data, formed by the rebinning operation, of each group in the direction of the connecting line,
    b) backprojecting the filtered data of a plurality of groups.

3. A computed tomography method as claimed in claim 1, in which the reconstruction step includes an inverse Fourier transformation.

4. The method claimed in claim 1 wherein continuous acquisition of measuring values for further CT images takes place while CT images are continuously being reconstructed.

5. A computed tomography apparatus, which apparatus includes:
    a) a radiation source for generating a conical radiation beam which traverses an examination zone or an object present therein,
    b) a drive device for realizing a circular relative motion, including a rotation about an axis of rotation, between the radiation source and the examination zone or the object,
    c) a detector unit for the acquisition of measuring values, during the relative motion, which measuring values are dependent on the intensity in the radiation beam to the other side of the examination zone,
    and also includes an image processing unit for generating at least one CT image from the measuring values by performing the steps of:
    d) rebinning the measuring values so as to form a number of groups, each group containing the measuring values of fan beams which are situated in fan beam planes which extend parallel to one another and to the axis of rotation, rays of the fan beams traverse a plane which extends perpendicular to the fan beam planes,
    e) reconstructing a spatial distribution of an attenuation of the radiation from the measuring values, by treating the fan beam rays of the parallel fan beam planes of the groups as parallel rays while reconstructing at least one CT image.

6. A computer readable media comprising a program for controlling a computed tomography apparatus to perform the steps of:
    a) causing a radiation source to generate a conical radiation beam which traverses an examination zone or an object present therein,
    b) causing rotation of the radiation source relative to the examination zone or the object about an axis of rotation,
    c) causing a detector unit to acquire measuring values which are dependent on the intensity in the radiation beam to an opposite side of the examination zone from the radiation source during the relative motion, d) rebinning the measuring values so as to form a number of groups, each group containing the measuring values, each group corresponding to fan beams situated in equidistant fan beam planes which extend parallel to one another, the fan beam planes of each group being perpendicular to a group plane which contains the axis of rotation, e) reconstructing a spatial distribution of an attenuation of the radiation from the measuring values by treating the measuring values as representing rays extending perpendicularly to the group plane of the corresponding group to form a continuously updated fluoroscopic CT image.

* * * * *